(12) United States Patent
Hall et al.

(10) Patent No.: US 10,590,117 B2
(45) Date of Patent: Mar. 17, 2020

(54) SPRING RETAINING PIN FOR VALVE STEM RETENTION

(71) Applicant: HUSKY INJECTION MOLDING SYSTEMS LTD., Bolton, Ontario (CA)

(72) Inventors: Douglas Oliver Hall, South Jefferonville, VT (US); Patrice Fabien Dezon-Gaillard, Jericho, VT (US); Manon Danielle Belzile, Fairfield, VT (US); Edward Joseph Jenko, Essex, VT (US); John Knapp, St. Albans, VT (US)

(73) Assignee: Husky Injection Holding Systems Ltd., Bolton, Ontario (CA)

( * ) Notice: Subject to any disclaimer, the term of this patent is extended or adjusted under 35 U.S.C. 154(b) by 399 days.

(21) Appl. No.: 15/320,970

(22) PCT Filed: Jun. 26, 2015

(86) PCT No.: PCT/US2015/037963
§ 371 (c)(1),
(2) Date: Dec. 21, 2016

(87) PCT Pub. No.: WO2016/003796
PCT Pub. Date: Jan. 7, 2016

(65) Prior Publication Data
US 2017/0190088 A1    Jul. 6, 2017

Related U.S. Application Data

(60) Provisional application No. 62/018,695, filed on Jun. 30, 2014.

(51) Int. Cl.
*C07D 413/04* (2006.01)
*C07D 213/62* (2006.01)
(Continued)

(52) U.S. Cl.
CPC .......... *C07D 413/04* (2013.01); *B29C 45/281* (2013.01); *B29C 45/2806* (2013.01);
(Continued)

(58) Field of Classification Search
CPC .......................... C07D 413/04; B29C 45/2806
See application file for complete search history.

(56) References Cited

U.S. PATENT DOCUMENTS 4,589,839 A * 5/1986 Kurumaji ................ B29C 45/17
264/328.11
5,454,708 A * 10/1995 Boenig .................. B29C 33/442
264/334

(Continued)

OTHER PUBLICATIONS

European Search Report, dated Jan. 22, 2018, 8 pages.

*Primary Examiner* — Leith S Shafi
*Assistant Examiner* — Nicholas R Krasnow

(57) ABSTRACT

An apparatus and method of coupling and decoupling a valve stem to an actuator are disclosed. In one embodiment, the actuator includes a moveable member that is coupled to the valve stem. One of the valve stem and the moveable member is a male coupling portion and the other of the valve stem and moveable member is the female coupling portion. The male coupling portion is nested within the female coupling portion. A retaining pin retains the male coupling portion with respect to the female coupling portion.

9 Claims, 14 Drawing Sheets

(51) Int. Cl.
*C07D 213/78* (2006.01)
*C07D 213/81* (2006.01)
*B29C 45/28* (2006.01)

(52) U.S. Cl.
CPC ......... *C07D 213/62* (2013.01); *C07D 213/78* (2013.01); *C07D 213/81* (2013.01)

(56) References Cited

U.S. PATENT DOCUMENTS

| | | | | |
|---|---|---|---|---|
| 5,474,440 | A * | 12/1995 | Gellert | B29C 45/27 264/328.15 |
| 5,894,025 | A * | 4/1999 | Lee | B29C 45/281 425/562 |
| 8,282,387 | B2 * | 10/2012 | Braun | B29C 45/2735 425/549 |
| 2002/0114860 | A1 * | 8/2002 | Sattler | B29C 45/281 425/564 |
| 2003/0151165 | A1 * | 8/2003 | Colonico | B29C 45/2806 264/328.1 |
| 2009/0155405 | A1 * | 6/2009 | Gunther | B22D 17/2023 425/549 |
| 2011/0018172 | A1 * | 1/2011 | Bouti | B29C 45/1775 264/328.15 |
| 2014/0126958 | A1 | 5/2014 | Zhang | |
| 2015/0151473 | A1 * | 6/2015 | Olaru | B29C 45/281 264/328.1 |
| 2016/0067901 | A1 * | 3/2016 | Bazzo | B29C 45/76 264/40.5 |
| 2016/0136854 | A1 * | 5/2016 | Galati | B29C 45/281 264/328.12 |

\* cited by examiner

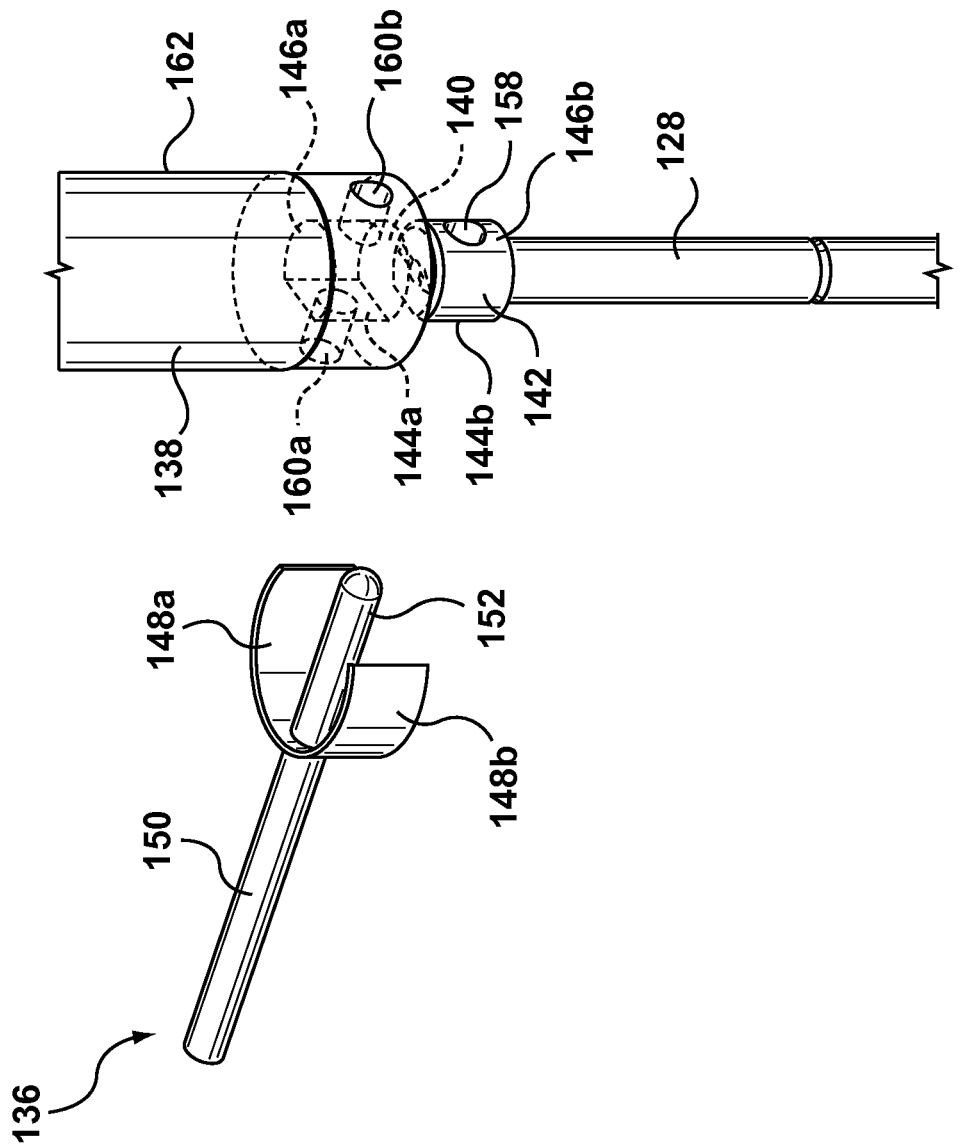

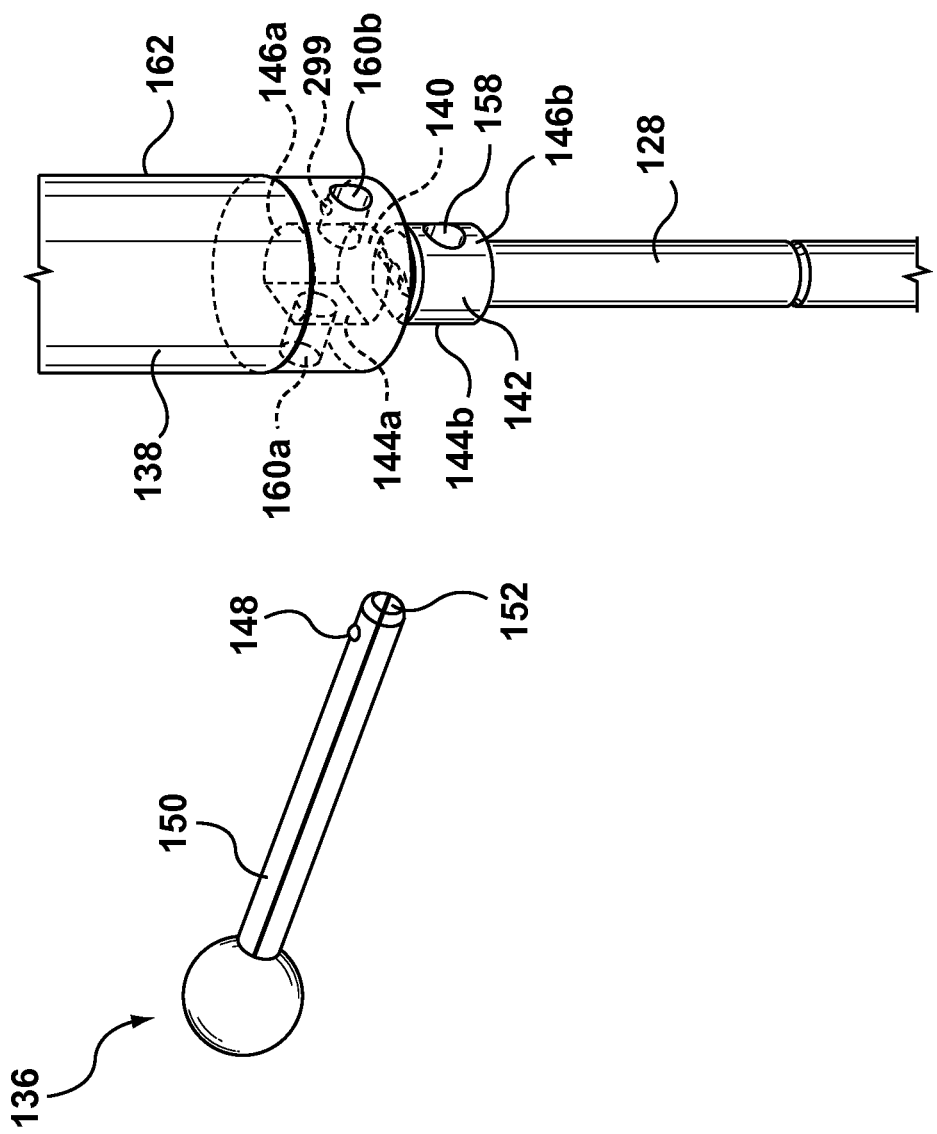

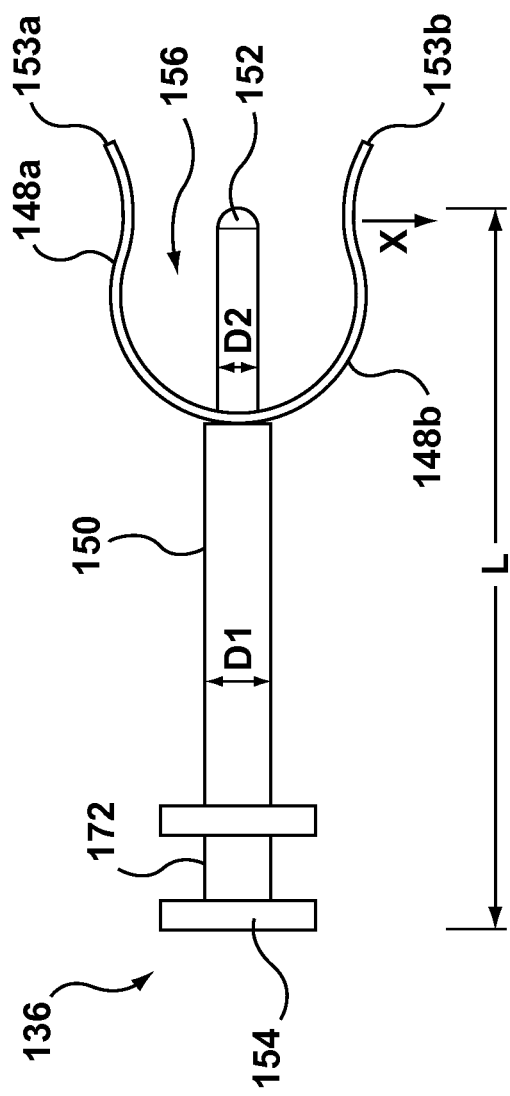
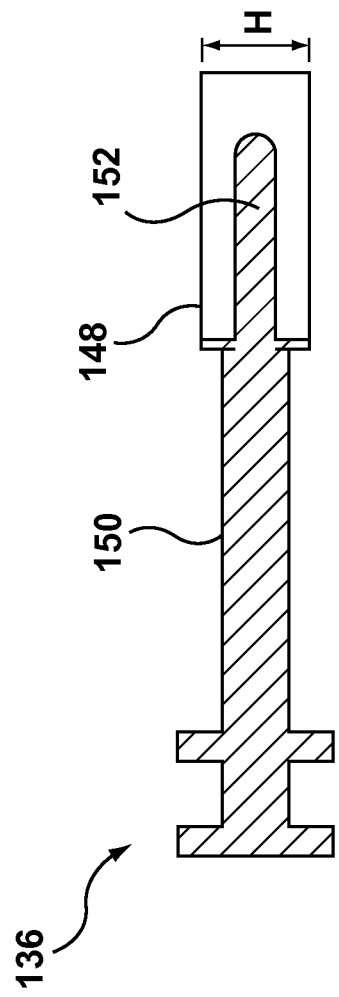
FIG. 3a
FIG. 3b

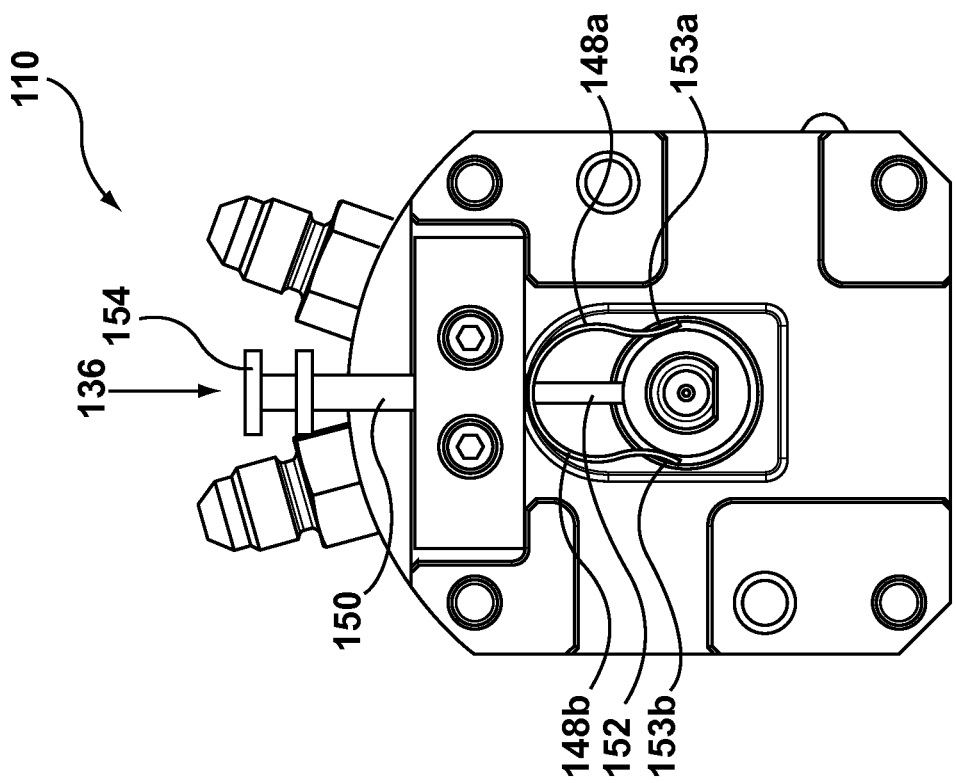
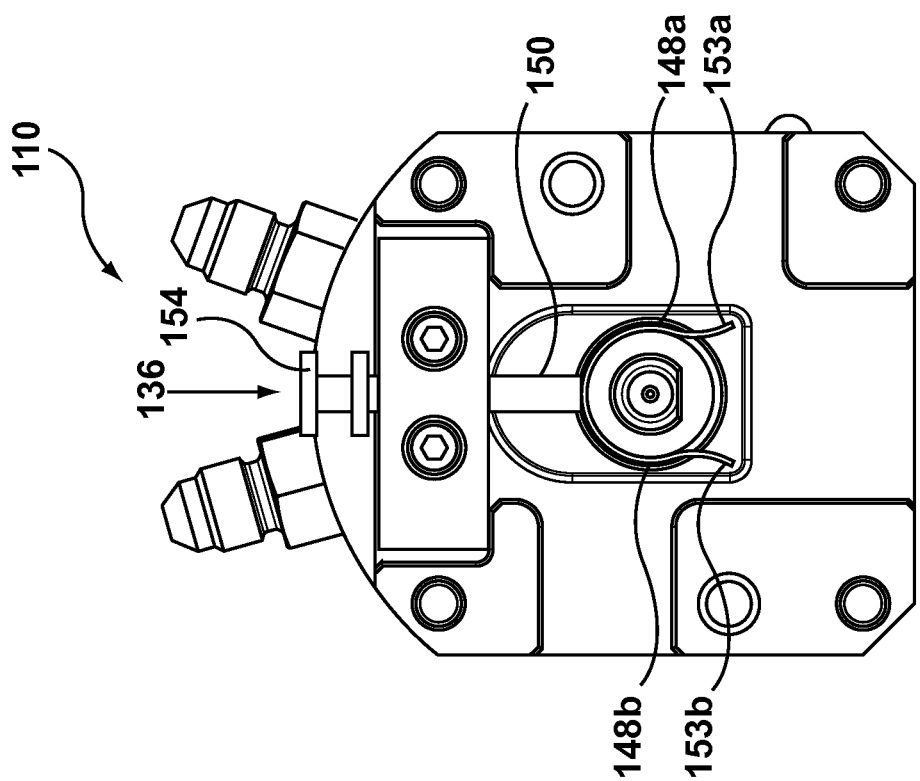

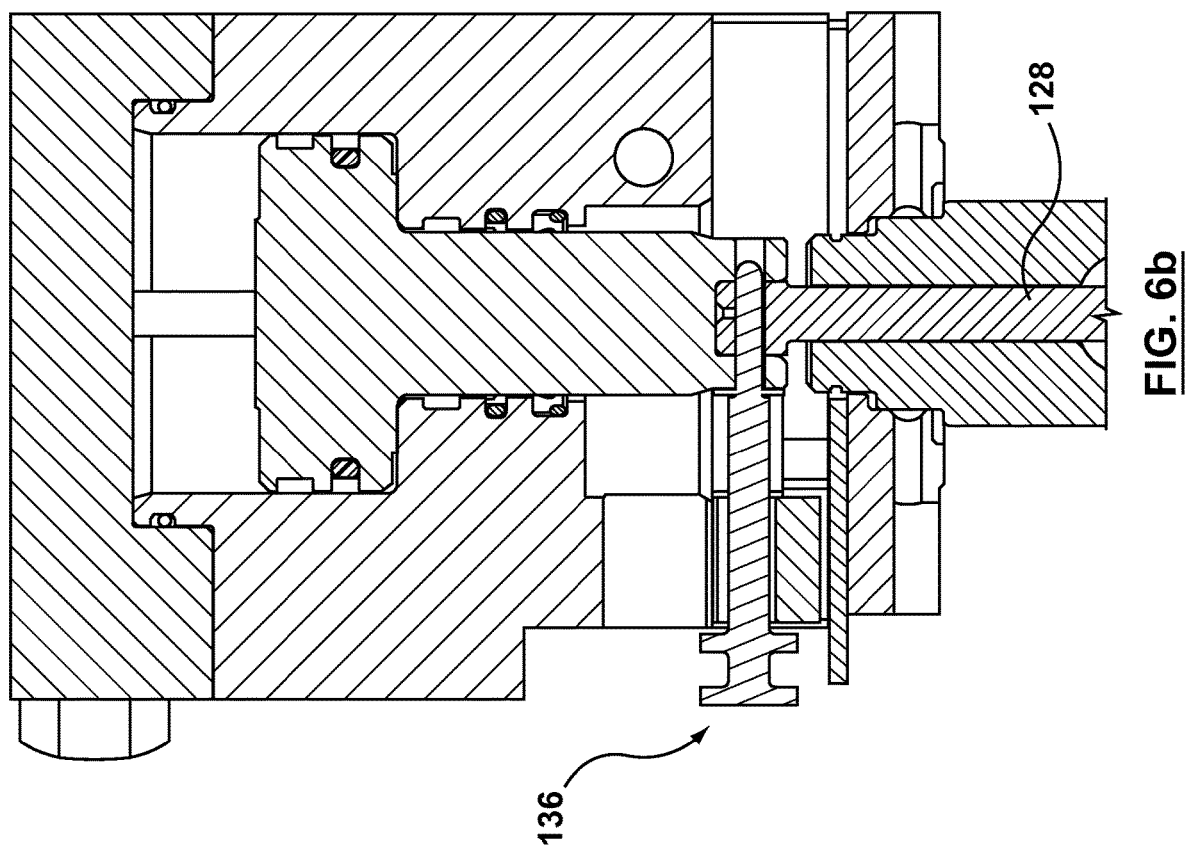

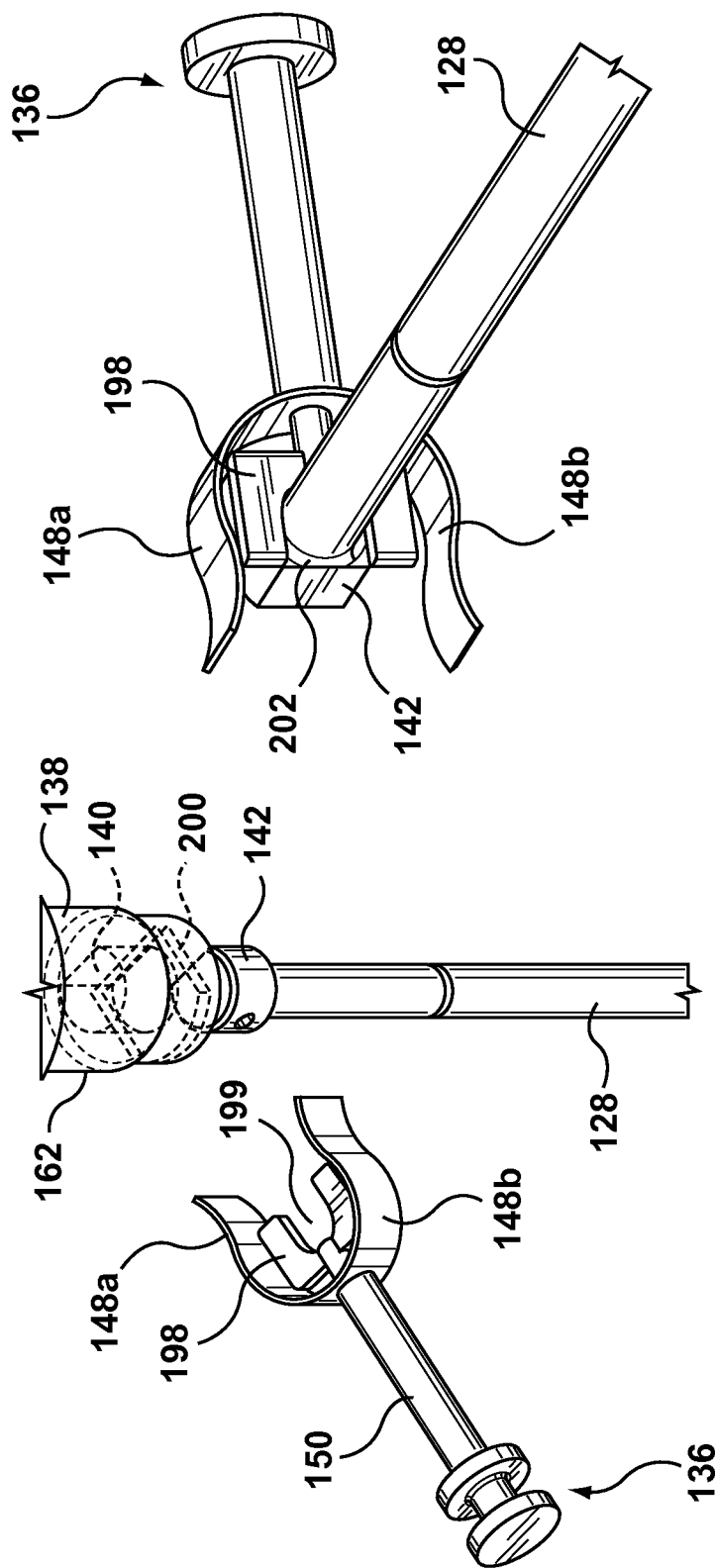

US 10,590,117 B2

SPRING RETAINING PIN FOR VALVE STEM RETENTION

FIELD

The disclosed embodiments are generally directed to molding material distributors for injection molding machines, such as hot runners, and more particularly to structures suitable for coupling and decoupling of a valve stem to an actuator.

BACKGROUND

Injection molding machines are used to produce plastic parts and some versions include mechanically gated nozzles (i.e., valve gated nozzles). Valve gated nozzles start and stop melt flow into the mold cavity by reciprocally moving the valve stem into open and closed positions, respectively. An actuator drives the valve stem between the open and closed positions and the valve stem is coupled to the actuator.

SUMMARY

In one embodiment, a valve gated molding material distributor for an injection molding machine for passing melt into a mold cavity is disclosed. The distributor includes a nozzle having a valve stem, an actuator configured to move the valve stem between a first position and a second position, the actuator having a moveable member coupled to the valve stem, and a retaining pin for coupling the valve stem directly to the moveable member.

In another embodiment, a method of using a valve gated hot runner including a valve stem and an actuator is disclosed. The actuator includes a moveable member, one of the moveable member and the valve stem comprising a male coupling portion and the other of the moveable member and the valve stem comprising a female coupling portion. The method includes nesting the male coupling portion within the female coupling portion and coupling the nested male and female coupling portions with a retaining pin to retain the male coupling portion relative to the female coupling portion.

In still another embodiment, a retaining pin for coupling a valve stem to a moveable member of an actuator of a molding material distributor is disclosed. The retaining pin includes an actuating end and an engaging end. The engaging end has an member engagement portion configured to engage the moveable member and an inner engagement portion configured to engage at least the valve stem.

It should be appreciated that the foregoing concepts, and additional concepts discussed below, may be arranged in any suitable combination, as the present disclosure is not limited in this respect.

The foregoing and other aspects, embodiments, and features of the present teachings can be more fully understood from the following description in conjunction with the accompanying drawings.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 2a is a perspective view of a valve stem decoupled from an actuator according to one embodiment;

FIG. 2b is a perspective view of a valve stem decoupled from an actuator according to another embodiment;

FIG. 3a is a top plan view of a retaining pin according to one embodiment;

FIG. 3b is a side plan view of the retaining pin of FIG. 3a;

FIG. 5a is a top view of an actuator with a retaining pin in an engaged position according to one embodiment;

FIG. 5b is a top view of the actuator of FIG. 5a with the retaining pin in a disengaged position;

FIG. 6b is a schematic cross-sectional view of FIG. 6a;

FIG. 10a is a perspective view of a valve stem decoupled from an actuator according to another embodiment; and FIG. 10b is a perspective view of a retaining pin coupled to the valve stem.

DETAILED DESCRIPTION

Figure 1:
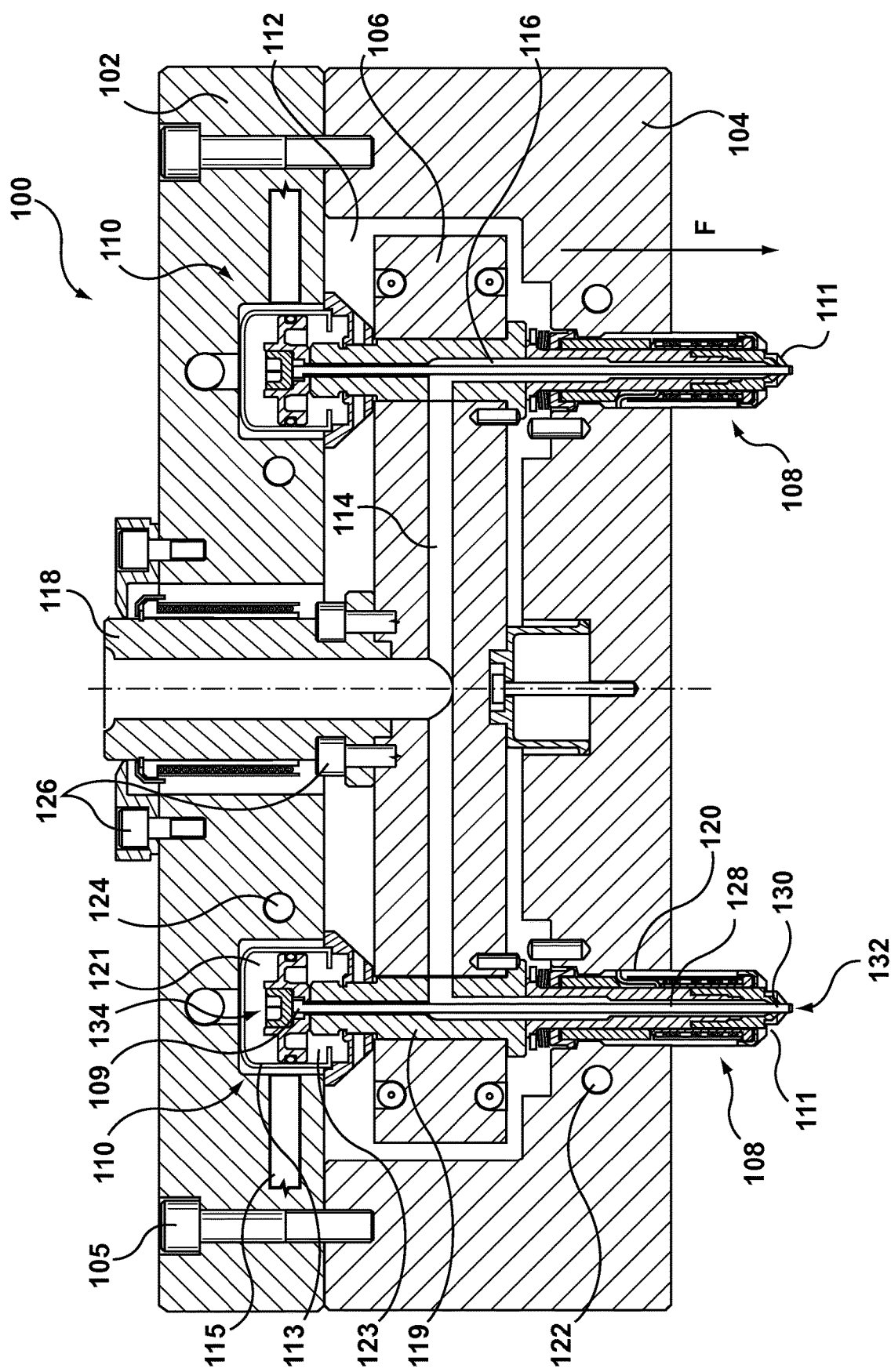
FIG. 1 is a cross-sectional schematic representation of a hot runner according to the prior art.

FIG. 1 shows a typical valve gated hot runner 100, which includes a first plate 102 (also known as a backing plate), a second plate 104 (also known as a mold plate), a manifold 106, valve gated nozzles 108, actuators 110, and melt channels 114. The first and second plates 102, 104 may be made from a steel alloy and coupled together, as is well known. Once coupled, the first and second plates 102, 104 define a manifold pocket 112, within which the manifold 106 lies. The manifold 106 includes one or more melt channel(s) 114 configured to convey the melt from an input that is usually connected with a sprue bushing 118 to an output (usually called a drop 116). The sprue bushing 118 may be coupled with a machine nozzle (known and not depicted) of an injection unit (known and not depicted). Although the manifold 106 is shown having two drops 116, it should be appreciated that the manifold 106 may have a single drop or may have multiple drops (or outputs).

The nozzle 108 is supportively received in the nozzle hole 120 of the second plate 104. The nozzle 108 may be operatively connected with the drop 116 of the manifold 106, so that the nozzle 108 may receive the melt from the drop 116. The nozzle tip 111 may also be received in a mold gate 132 of a mold assembly (known but not depicted) so that melt may flow from the nozzle 108 to a mold cavity (via the mold gate 132) of the mold assembly. Although two nozzles 108 are shown in this figure, one of skill in the art will appreciate that the hot runner 100 may include one nozzle 108 or multiple nozzles 108.

As is well known, a valve stem 128 is associated with the valve gated nozzle 108 such that it may be selectively moved between a retracted open position and a forward closed position, though valve gate nozzles have been developed where the valve stem is retracted to close and advanced to open. As such, embodiments described herein are not limited to the direction of valve stem closure.

The valve stem 128 extends from the backing plate 102 to a mold cavity (not shown), and an upstream end 109 of the valve stem 128 is connected to the actuator 110. A person having ordinary skill in the art will appreciate that the actuator 110 may be a pneumatic, hydraulic, or electric actuator. As is shown in the example of FIG. 1, the actuator 110 may have a cylinder 113 within which a piston 134 is disposed. The cylinder 113 includes a compression chamber 121 adjacent a first side of the piston 134 and an extension chamber 123 adjacent a second side of the piston 134. The actuator is connected to a fluid source 115, which may include a fluid, such as hydraulic fluid, air or other gas. When fluid pressure is applied to the compression chamber 121, the piston 134 is advanced (downward in this figure), which, in this example, forces the valve stem 128 into a closed position. When the fluid pressure is released, the valve stem 128 returns to an open position either by a return spring (not shown) or by fluid pressure being applied to the extension chamber 123.

Figure 9:
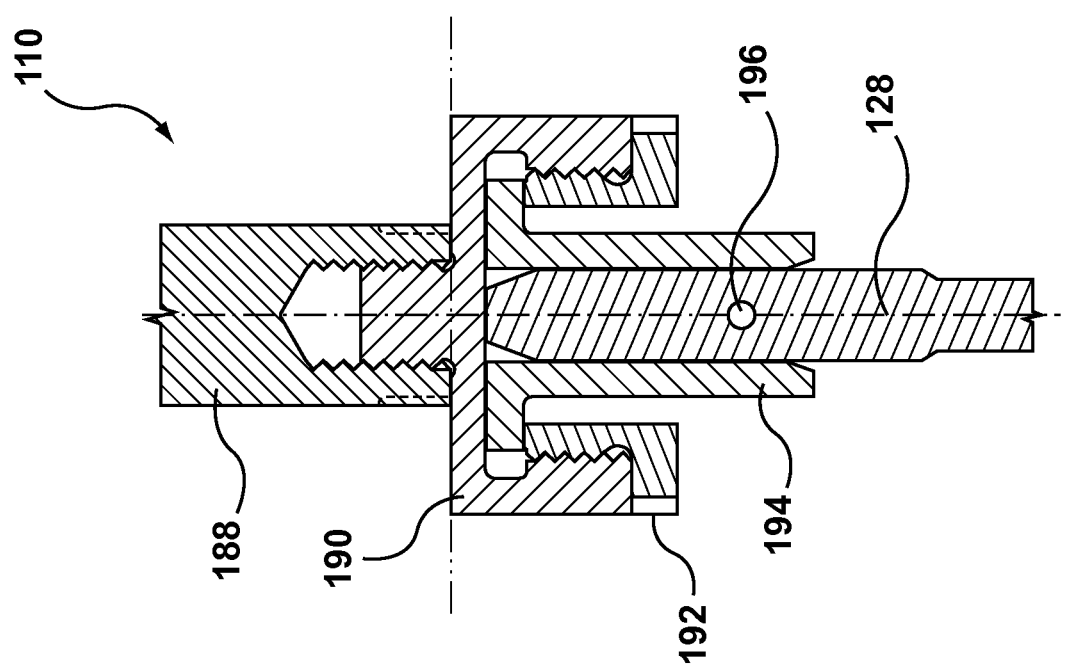
FIG. 9 is a schematic view of a valve stem coupled to an actuator according to another embodiment.

In some embodiments, the hot runner may have an electric actuator 110 to drive valve stem 128 movement. As shown in FIG. 9, in such an embodiment, the actuator 110 may have ball screw 188, a double threaded adaptor 190, a stem head retainer 192, and a stem sleeve 194. As is shown in this figure, the valve stem 128 is coupled to the actuator 110 via the stem sleeve 194. The actuator 110 may have a motor (not shown) that drives the valve stem 128. In some embodiments, the motor creates a rotary motion that is converted to linear motion via the ball screw 188, which drives linear motion of the valve stem. In one embodiment, the motor may be a brushless servomotor, however, a person having ordinary skill in the art will appreciate that other suitable motors may be used to drive valve stem movement, such as a linear motor.

When the valve stem is in the open position or configuration, melt is free to flow from the melt channel 114 to outlet 116 and mold cavity (not shown). Correspondingly, when the valve stem is in the closed position or configuration, the downstream end 130 of the valve stem 128 blocks a gate 132 to selectively substantially prevent melt flow from the melt channel 114 to the outlet 116.

Valve stems 128 are coupled to the actuator 110 in a variety of different ways. In some hot runners, the valve stem 128 is slideably engaged with the actuator (e.g., by sliding the head of the valve stem into a slot located in the actuator or piston). However, having a slotted connection requires that the actuator be lowered to the manifold and then slid to engage the head of the valve stem. Additionally, manufacturing a valve stem with a larger head and manufacturing a piston with a slot is more costly. This method also requires that either the stem or the piston fracture should a valve stem become frozen in the closed attitude.

According to one aspect of the invention, a retaining pin is used to couple the valve stem to the actuator. In some embodiments, the retaining pin is configured to retain the valve stem with respect to the actuator, or to a moveable member of the actuator. With this design, the valve stem may be retained with respect to the actuator while a molding material distributor, such as the hot runner, is in use and may also be removable from the actuator when the hot runner is not in use or when the hot runner needs to be serviced. In some embodiments, the valve stem may be decoupled at any point in stroke position (e.g., any position between the open and closed positions). The retaining pin may also be configured to maintain the connection between the retaining pin and the actuator without any additional components. This design may also allow for a tool free assembly and disassembly of the hot runner and for disengagement of the retaining pin without the removal of any other component. In some embodiments, the retaining pin is removable. The retaining pin may also be designed to have any one of numerous shapes for coupling the valve stem to the actuator and to move with the actuator movement.

In some embodiments, the actuator includes a moveable member that is coupled to the valve stem. In these embodiments, one of the moveable member and the valve stem includes a male coupling portion and the other of the moveable member and the valve stem includes a female coupling portion. In other embodiments, each of the valve stem and the moveable member has a male coupling portion and a female coupling portion. In use, the male coupling portion is nested within the female coupling portion and the retaining pin retains the male coupling portion relative to the female coupling portion.

FIGS. 2a and 2b are exploded views of different embodiments of the valve stem 128 decoupled from the actuator (not shown). These figures are examples in which the moveable member 138 includes a female coupling portion and in which the valve stem 128 includes a male coupling portion. As is shown in these figures, the moveable member 138 includes a recess 140 into which the head 142 of the valve stem 128 is nested. The shape and size of the recess 140 of the moveable member 138 may correspond to the shape and size of the head 142 of the valve stem 128. A person having ordinary skill in the art will appreciate that any suitable shape and size of the recess 140 and of the valve stem head 142 may be used as this aspect of the disclosure is not limited in this regard. For example, the valve steam head 142 and the recess 140 may have a circular, oval, rectangular, square or triangular shape.

In some embodiments, as is shown in FIGS. 2a and 2b for example, the recess 140 and the valve stem head 142 have a D-shaped configuration, that is the recess 140 and valve stem head 142 have one flat side 144 and one curved side 146. In such embodiments, precise placement of the valve stem in the hot runner may be achieved as only the flat side 144b of the valve stem head 142 may be engaged with the flat side 144a of the recess 140. This D-shaped configuration may also prevent the valve stem 128 from rotating once the valve stem 128 is nested in and coupled to the piston 134, and may further allow a customer to contour the downstream end (not shown) of the valve stem 128 to conform to the cavity and/or gate shape (not shown) and to maintain the shape relationship between the valve stem 128 and cavity.

In some embodiments, the retaining pin 136 includes one or more grips 148 and a pin 150. In these embodiments, the pin 150 functions to retain the valve stem with respect to the actuator 110 or to the moveable member 138 of the actuator 110. Further, as the pin extends through the moveable member 138 and the valve stem 128, as will be described below, the pin functions to limit or prevent rotation of the valve stem 128 with respect to the moveable member 138 and thus, the actuator 110. The one or more grips 148 also serve to limit or prevent rotation in the hot runner. As will be described, the one or more grips 148 engage with the moveable member 138 and, thus, limit or prevent rotation of the moveable member with respect to the actuator 110. In some embodiments, the one or more grips 148 limit rotation of the moveable member about an axis of the pin 150 of the retaining pin 136.

FIG. 2a depicts an embodiment in which there are two grips 148a, 148b extending outwardly from the pin 150 like arms. The two grips 148a, 148b are intended to grip onto or clip over the movable member 138 when the retaining pin 136 is coupling the movable member 138 with the valve stem 128.

With reference to the embodiment shown in FIG. 2a, and as shown in FIGS. 3a and 3b, a first end 152 of the pin 150 may extend between the grips 148. The pin 150 may have different diameters (see, e.g, D1 and D2) along a length L of the pin 150 in some embodiments, although a person having ordinary skill in the art will appreciate that the pin may also have the same diameter along the length L of the pin. Additionally, although the pin 150 (including the first end 152 of the pin) is shown as having a substantially circular cross-sectional shape in these figures, the pin 150 may have other suitable shapes. For example, the pin 150 may have a rectangular, square, triangular, oval or other polygonal cross-sectional shape suitable for retaining the valve stem 128 with respect to the moveable member.

As is shown in FIGS. 2a and 3, the retaining pin 136 may include two grips 148a, 148b, although the retaining pin 136 may also have one or more grips 148 in some embodiments. As shown in the embodiment of FIG. 3, each grip 148 can extend outwardly from the pin 150 (and may resemble arms of a clip). The grips 148 can each include a leading edge 153, which may facilitate engagement of the grips 148 with the moveable member 138, as will be described. In some embodiments, the grips 148 are configured such that a height H of the grips 148 stabilizes the retaining pin 136 against the moveable member 138. That is, the height of the grips may be configured to provide structural integrity to the retaining pin 136 when engaged with the moveable member 138. In some embodiments, the grips 148 of the retaining pin 136 prevent rotation of the moveable member 138 about the lengthwise axis of the pin 150 when the retaining pin 136 is in an engaged and/or disengaged position. For purposes herein, a "disengaged position" may mean a position in which the retaining pin is not engaged with at least one of the moveable member and the valve stem such that the valve stem is removable from the moveable member. Although the grips 148 are shown as having the same design in FIG. 3a, a person having ordinary skill in the art will appreciate that in other embodiments the design (e.g., the shape and radius) of the first grip 148a may differ from the design of the second grip 148b. In some embodiments, the grips 148 may be wires or may be circular in cross section. The pin may also have a visual indicator 154 of the retaining pin's 136 position, as described below.

The grips 148 in FIG. 2a may be referred to as arms of a clip.

Figure 6A:
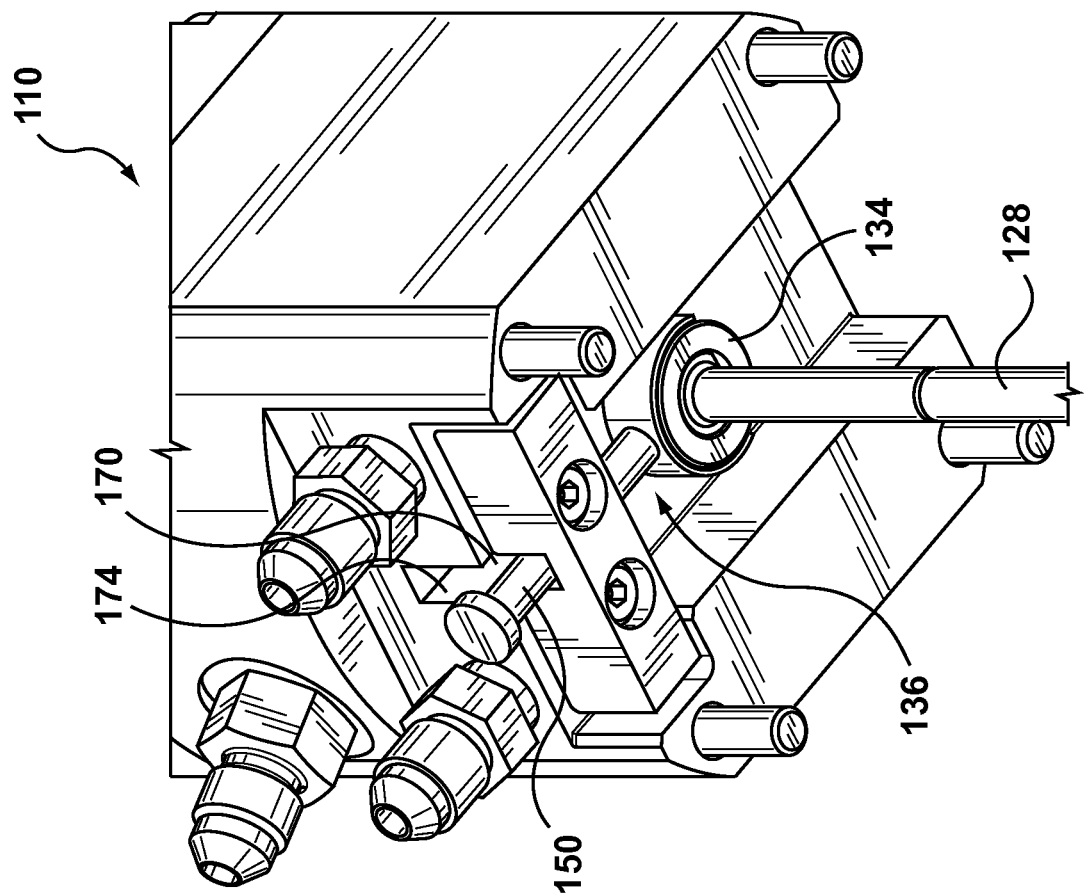
FIG. 6a is a perspective view of a valve stem coupled to an actuator according to one embodiment.

As shown in FIG. 3a, in one embodiment, the grips 148 of the retaining pin 136 have a substantially U-shaped configuration. The grips 148 may also have a substantially C-shaped configuration, as shown in FIG. 6a, or another suitable-shaped configuration. In some embodiments, the grips 148 form an opening 156, and in some embodiments, the shape of the opening 156 corresponds with the shape of the female coupling portion, which, as shown in FIG. 2 is the moveable member 138. The opening 156 may be substantially D-shaped, U-shaped, C-shaped, or have another suitable shape.

The grips 148 may be configured to move outwardly as the retaining pin 136 is engaged with the moveable member 138 and then to return to their original position to capture the moveable member 138. In some embodiments, the leading edges 153 of the grips 148 facilitate the outward movement of the grips 148. As is shown, in some embodiments, the leading edges 153 of the grips 148 form flared ends of the U-shaped configuration. In use, when the retaining pin 136 is pushed towards the moveable member 138, the leading edges 153 contact the moveable member 138, which cause outward camming of the leading edges 153, and, thus, the grips (see, e.g., direction X). In some embodiments, the flared ends or reverse curves of the leading edges 153 provide a narrowing of the opening 156 for the camming action. Once the moveable member 138 is fully seated in the opening 156, the leading edges 153 may return partially or fully to their original position, thereby gripping the movable member 138.

FIG. 2b depicts an embodiment in which there is one grip 148 on the retaining pin 136. In this embodiment the grip 148 is a ball lock, and the retaining pin 136 forms a ball lock pin. In a further exemplary embodiment (not shown), there may be two grips 148 on the retaining pin 136 in which each of the two grips is a ball lock. The two grips 148 can be on opposite sides of the retaining pin 136. The ball lock can be a spring operated ball lock that can be pushed into the pin 150 but that is biased to be extending partially out of the pin 150.

As shown in FIGS. 2a and 2b the valve stem head 142 has a hole 158 extending through the valve stem head 142. In this embodiment, the hole 158 of the valve stem head 142 extends transversely through the valve steam head 142, although a person having ordinary skill in the art will appreciate that the location, position and orientation of the hole 158 may vary in other embodiments. Additionally, although only one hole 158 is shown in the valve stem head 142, a person having ordinary skill in the art will appreciate that the valve stem head 142 may have more than one hole 158 in other embodiments.

FIGS. 2a and 2b also illustrates the holes 160 in the moveable member 138, which extend outwardly from the recess 140 to an exterior surface 162 of the moveable member 138. As with the valve stem head 142, the holes 160 in the moveable member 138 extend transversely with respect to the moveable member 138, although they may have other suitable locations, positions and orientations. Additionally, although two holes 160a, 160b are shown in the moveable member 138 in this embodiment, a person having ordinary skill in the art will appreciate that in other embodiments the moveable member 138 may have only one hole 160 or may have more than two holes 160.

With reference to the embodiment in FIG. 2b, the interior of the hole 160 (or the interior surface of the hose 160) in the movable member 138 has or defines an indentation 299. The indentation 299 is sized to receive or engage with the ball lock grip 148 when the retaining pin 136 is coupling the movable member 138 with the valve stem 128. The ball lock (i.e. the grip 148 in this embodiment) can move between a locked position and an unlocked position. The ball lock is biased towards the locked position. In the locked position the ball lock partially extends or protrudes out of the pin 150. In the unlocked position the ball lock is retained in the pin 150. This action or biasing of the ball lock can be performed with a spring or other biasing member. The indentation 299 is positioned and sized to receive the ball lock when the ball lock is in the locked position. In this way the ball lock is removably engageable with an indentation 299 in the female coupling portion (or the movable member 138).

With continued reference to the embodiment in FIG. 2*b*, the retaining pin 136 or the holes 158, 160 (or both) are sized such that there is not enough space for the ball lock to be in the locked position when the retaining pin 136 is inside of the holes except when the ball lock is aligned with the indentation 299. The ball lock is biased (e.g. with a spring or other similar mechanism) to be in the locked position. The force of the biasing action can be overcome with a predetermined amount of force in order to insert or remove the retaining pin 136 into the engaged position. When the retaining pin 136 in this embodiment is coupling the movable member 138 with the valve stem 128 the ball lock is in the locked position and is extended into the indentation 299 thereby securing the retaining pin 136 in relation to the movable member 138.

FIGS. 4-8 show various embodiments in which the moveable member is the piston 134 of the actuator 110, with the valve stem 128 being coupled to the piston 134 via retaining pin 136 (see, e.g., FIGS. 6*a* and 6*b*). In these embodiments, the piston 134 is configured to be the female coupling portion and the valve stem 128 is configured to be the male coupling portion. Thus, as is shown and as with the previous examples, the piston 134 includes a recess 140 into which the valve stem head 142 is nested, and the valve stem head 142 and the piston 134 include holes 158, 160 extending transversely through the valve stem 128 and piston 134, respectively.

Figure 4:
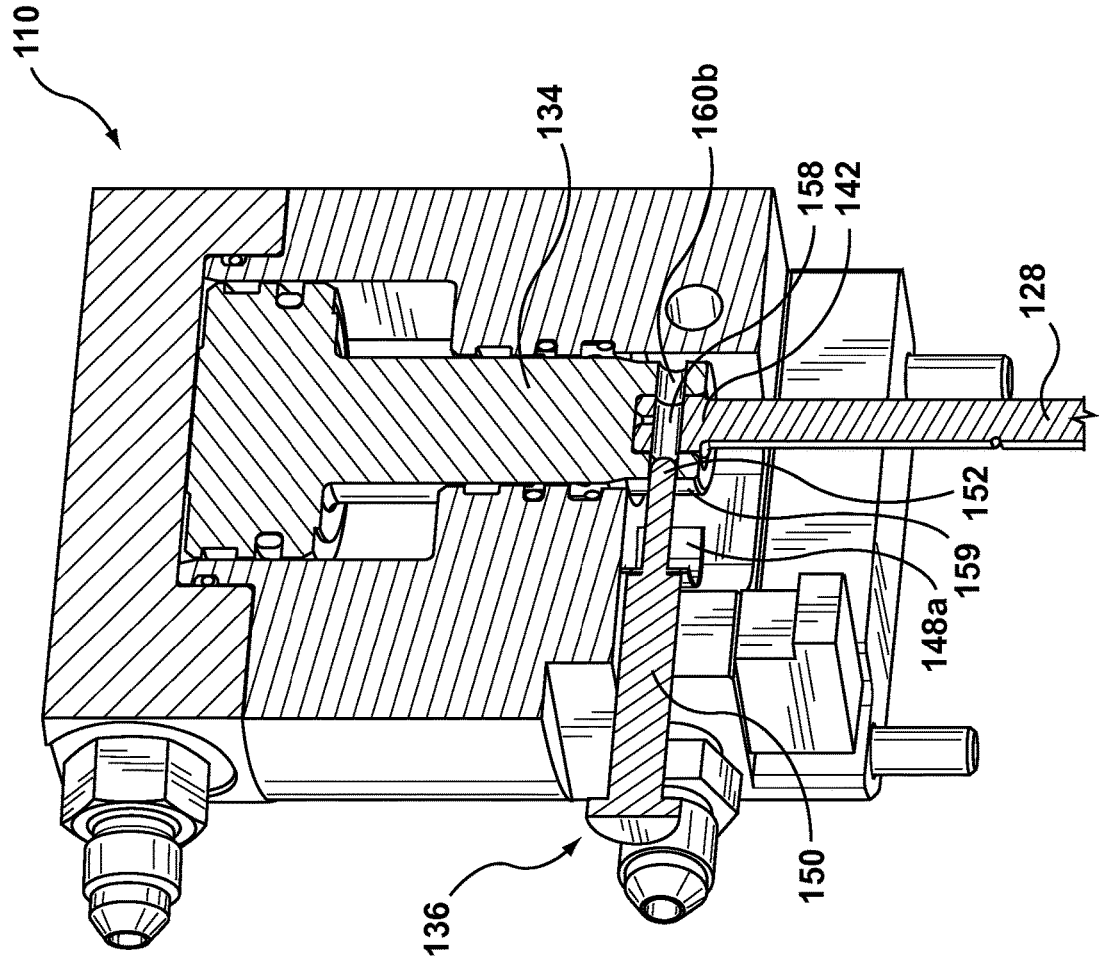
FIG. 4 is a perspective cross-sectional view of a valve stem nested within an actuator according to another embodiment.

In use, when the valve stem head 142 is nested within the piston 134, the holes 160*a*, 160*b* in the piston 134 align with the hole 158 in the valve stem head 142. This alignment may be seen, for example, in FIG. 4. Next, the retaining pin 136 is engaged to secure the valve stem 128 to the piston 134. During engagement, the first end 152 of the pin 150 is inserted through the holes 160, 158 of the piston 134 and the valve stem head 142, respectively. In some embodiments, as is shown in FIG. 4, the first end 152 of the pin 150 is first inserted through the hole 160*a* in the piston 134 and is then inserted through the hole 158 in the valve stem head 142. In some embodiments, the pin 158 is inserted via a front side of the actuator 110. While the pin 150 is being inserted into the holes 160, 158 of the piston 134 and valve pin head 142, respectively, the one or more grips 148 of the retaining pin 136 are being engaged with the of the piston 134.

For example, in accordance with the embodiment of FIGS. 2*a*, 3*a* and 3*b*, while the pin is being inserted into the holes 160, 158 of the piston 134 and the valve pin head 142, respectively, the grips 148 of the retaining pin 136 are being engaged with the exterior surface 159 of the piston 134. When the retaining pin 136 is engaged with the piston 134, the piston 134 is captured in the opening 156 by the grips 148.

By way of further example, in accordance with the embodiment of FIG. 2*b*, while the pin is being inserted into the holes 160, 158 of the piston 134 and the valve pin head 142, respectively, the grip 148, which in this embodiment is the ball lock, is pushed into the unlocked position so that the pin 150 can move within the holes 160, 158. When the pin 150 reaches the position in which the grip 148 is aligned with the indentation 299 in the hole 160, then due to the grip's 148 biasing action the grip 148 moves to the locked position and into the indentation 299. When the grip 148 (in this embodiment the ball lock) is in the indentation 299 the retaining pin 136 is engaged with the piston 134.

In some embodiments, as shown in FIG. 4, the hot runner is configured such that the first end 152 of the pin 150 is always engaged with the piston 134. That is, in the disengaged position, the first end of the pin remains engaged with one of the holes 160*a* in the piston 134. In such an embodiment, engagement of the retaining pin 136 only requires the first end 152 of the pin 150 to be inserted into the hole 158 of the nested valve pin head 142.

In some embodiments, the hot runner is configured such that the grips 148 of the retaining pin 136 always remain engaged with the piston 134. For example, as shown in FIGS. 5*a* and 5*b*, (and using an embodiment of the retaining pin 136 such as shown in FIG. 2*a*) the grips 148 are engaged with the piston 134 when the retaining pin is in the engaged position, and the leading edges 153 of the grips 148 are engaged with the piston 134 when the retaining pin 136 is in the disengaged position. In some embodiments, as shown in FIG. 5*a*, when the retaining pin 136 is in the engaged position, the leading edges 153 of the grips 148 are moved past the piston 134 and, thus, are not engaged with the piston 134. As shown in FIG. 6*a*, in other embodiments, the leading edges 153 of the retaining pin 136 are configured to engage with the piston 134 when the retaining pin 136 is in the engaged position. In some embodiments, this constant engagement between the retaining pin 136 and the piston 134 prevents rotation of the piston 134 when the retaining pin 136 is in the engaged and disengaged positions.

Figure 7A:
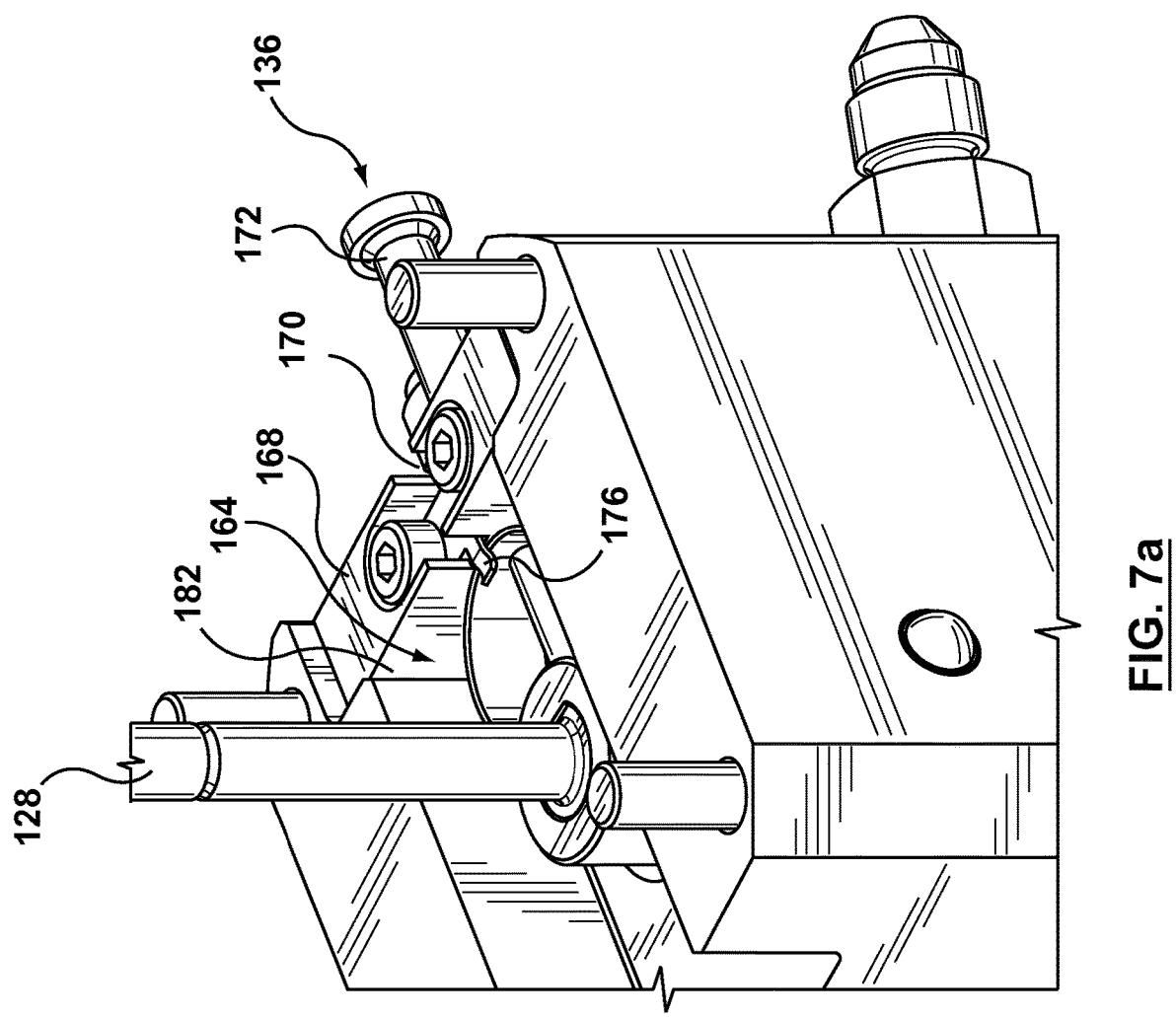
FIG. 7a is a perspective view of a retaining pin being retained by a retention block according to one embodiment.

In some embodiments, as is shown in FIG. 7*a*, the actuator has a retention block 168 for retaining the retaining pin 136 when the retaining pin 136 is in the disengaged position. Stated differently, the retention block 168 assists in arresting the retaining pin's 136 motion away from the piston 134 (or other moveable member 138). The retention block also assists in aligning the retaining pin 136 with respect to the piston 134. Additionally, in embodiments in which the retaining pin 136 is always engaged with the piston 134, the retention block 168 maintains the retaining pin 136 in a position such that the one or more grips 148 and the first end 152 of the pin 150 remain in contact with piston 134, even when the retaining pin 136 is in the disengaged position.

As is shown in FIG. 7*a*, the retention block has a hole 170 through which a second end 172 of the pin 150 extends. In some embodiments (see, e.g., FIG. 6*a*), the hole 170 of the retention block 168 is sized to allow the retaining pin 136 to move with the coupled valve stem 128 and piston 134 (or other moveable member) between the open and closed position (e.g., throughout the stroke of the valve stem 128). In some embodiments, as shown in FIG. 6*a*, the hole 170 of the retention block 168 cooperates with a hole 174 in the actuator 110 to allow the retaining pin 136 to travel with the coupled valve stem 128 and piston 134. This may also allow the retaining pin to be accessible throughout valve stem 128 travel and further may allow the retaining pin to be disengaged and, thus, the valve stem to be decoupled, at any point in stroke position.

As shown in FIG. 7*a*, in some embodiments, the actuator is configured with a pocket 164 that extends at least between an interior side 182 of the retention block 168 and the piston 134 (or other moveable member). In some embodiments, the pocket 164 is sized to allow the retaining pin 136 to move with the moveable member once disengaged. The pocket 164 may also be sized to allow the retaining pin 136 to be retracted into the disengaged position while maintaining engagement between retaining pin 136 and the piston 134 (e.g., between the first end 152 of the pin 150 and the leading edges 153 of the grips 148 and the piston 134 in accordance with the embodiment of the retaining pin 136 shown in FIG. 3). The pocket 164 may cooperate with the retention block 168 to maintain proper position and alignment of the retaining pin 136. In some embodiments, as is shown in FIG. 7*d*, the actuator also has channels 166 into which the leading edges 153 of the grips 148 are maintained when the retaining pin 136 is in the engaged position. The channels 166 may facilitate movement of the retaining pin 136 as the leading edges 153 of the grips are guided into the channels 166.

Figure 7C:
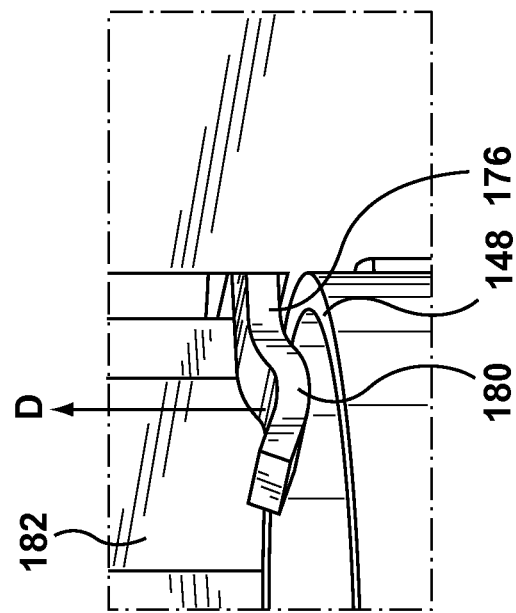
FIG. 7c is a perspective view of a retention block detent according to another embodiment.
Figure 7B:
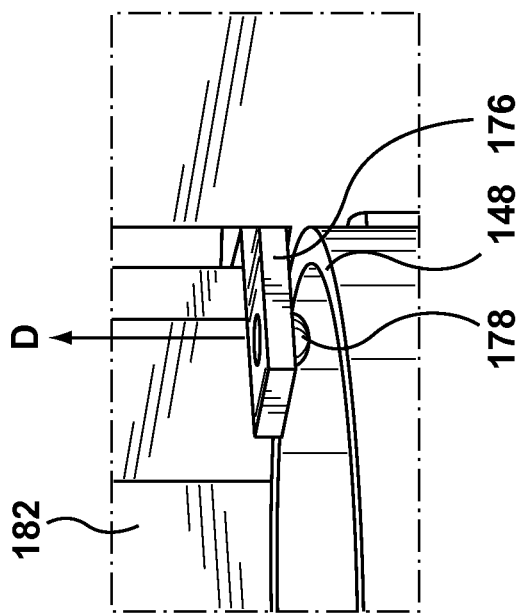
FIG. 7b is a perspective view of a retention block detent according to one embodiment.
Figure 7D:
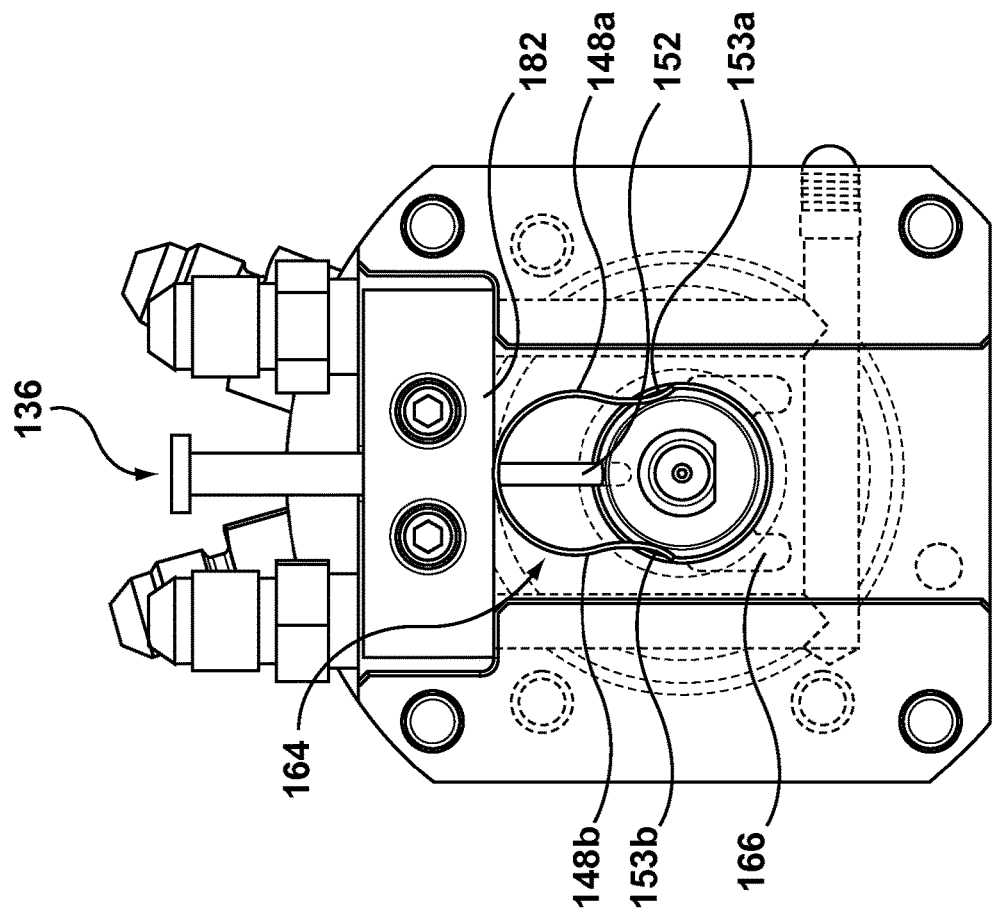
FIG. 7d is a top view of an actuator according to another embodiment.

As illustrated in FIGS. 7a-7c, in one example, the retention block has a detent 176 for retaining the retaining pin 136 in the disengaged position. In use, (and in accordance with certain embodiments of the retaining pins 136, such as that shown in FIG. 3) when the retaining pin is moved to the disengaged position, the detent 176 engages with the grip 148 to retain the retaining pin 136 in the disengaged position. In one embodiment, shown in FIG. 7b and using the embodiment of the one or more grips 148 shown in FIG. 2a, the detent 176 has a dimple 178. When the grip 148 contacts the dimple 178, the detent 176 may move in a direction D, after which point the detent 176 returns to its original position to trap the grip 148 between the interior side 182 of the retention block 168 and the dimple 178. Alternatively, in another embodiment, the detent 176 may remain stationary and the retaining pin 136 may move in a direction opposite direction D to move past the dimple 178 and be retained between the dimple 178 and the interior surface 182 of the retention block 168. In another embodiment, instead of a dimple, the detent 176 may have an arcuate portion 180 (see, e.g., FIG. 7c). As with the previous example, in use, the arcuate portion may move in the direction D when the grip 148 contacts the arcuate portion 180, after which point the detent 176 may return to its original position, thus trapping the grip 148 between the interior side 182 of the retention block 168 and the actuate portion 180 of the detent 176. Alternatively, like the previous example, the detent 176 may remain in place and instead the retaining pin 136 may move in a direction opposite direction D to move past the arcuate portion 180 and to be retained between the arcuate portion 180 and the interior surface 182 of the retention block 168.

In embodiments in which the detent 176 moves, the detent 176 may include a resilient material which allows the detent 176 to move in direction D and then return to its original position. A person having ordinary skill in the art will appreciate that the detent 176 need not move a substantial distance in direction D when the grip 148 contacts the dimple 178 or arcuate portion 180. Instead, the detent 176 need only move slightly (e.g., the height of the dimple 178 or the height of the arcuate portion 180) to allow the grip 148 to travel past the dimple 178 or the arcuate portion 180. It is understood that only certain embodiments of the retaining pin 136 can be used with the detent 176. For example, the retaining pin 136 shown in FIG. 2b may be such that the detent 176 cannot engage or does not engage with the grip 148. Accordingly, the embodiments illustrated in FIGS. 7a to 7c may not include (or be used with) the retaining pin 136 as shown in FIG. 2b.

Figure 8:
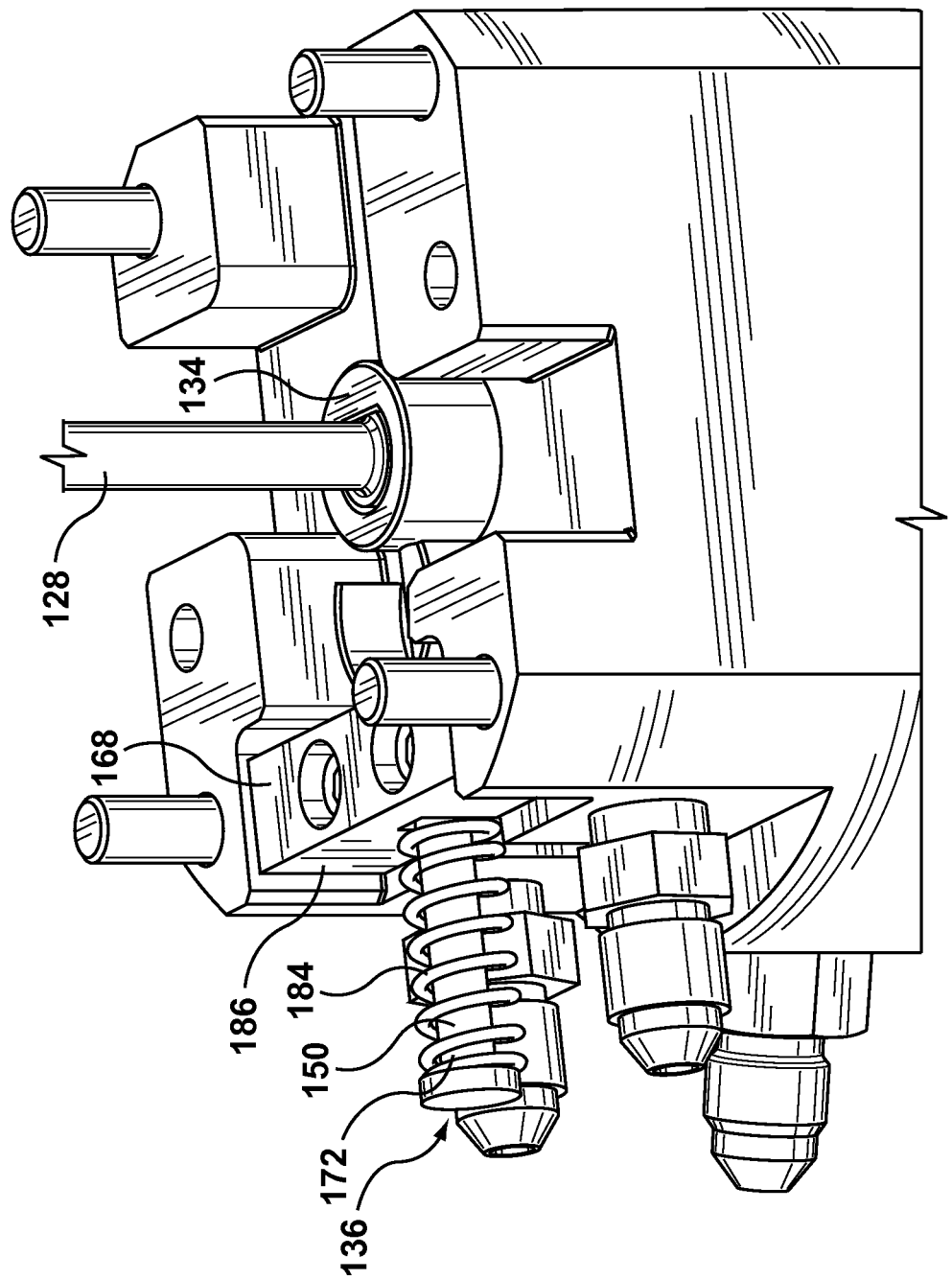
FIG. 8 is a perspective view of a valve stem nested within the actuator and a retaining pin in a disengaged position according to one embodiment.

In some embodiments, as is shown in FIG. 8, instead of using a detent to retain the retaining pin in the disengaged position, a spring 184 is placed around the pin 150 of the retaining pin 136, between an exterior surface 186 of the retention block 168 and the second end 172 of the pin 150. The spring 184 biases the retaining pin 136 in the disengaged position. In use, once the retaining pin 136 is decoupled from the valve stem 128 (e.g., by removing the first end 152 of the pin 150 from the hole 158 in valve stem head 142), the retaining pin 136 is returned to the disengaged position.

Although the actuator is shown and described as having a retention block 168 for retaining the retaining pin 136, in some embodiments, the actuator 110 does not have a retention block 168. In such an embodiment, once the retaining pin is disengaged from the moveable member 138 and valve stem 128, the retaining pin 136 can be removed from the hot runner 100 until the valve stem 128 is again coupled to the moveable member 138.

As previously mentioned, in some embodiments, the retaining pin 136 includes a visual indicator 154 to indicate whether the retaining pin 136 is in the engaged or disengaged position. As is shown in FIG. 5a, when the retaining pin 136 is in the engaged position, the visual indicator 154 is hidden from a top view of the actuator 110. In contrast, when the retaining pin 136 is in the disengaged position, the visual indicator 154 is visible, as is shown in FIG. 5b. In some embodiments, the visual indicator 154 is used to disengage the retaining pin 136. For example, in one embodiment, a tool such as a screwdriver is leveraged against the visual indicator 154 to move the retaining pin into the disengaged position.

FIG. 9 illustrates an embodiment in which the moveable member is the stem sleeve 194 of the electric actuator 110. As with the previous embodiments involving the piston 134, in this embodiment, the stem sleeve 194 is the female coupling portion into which the valve stem 128 is nested and to which the valve stem 128 is coupled via retaining pin 136 (not shown). As is shown, the valve stem 128 has a hole 196 extending through a body of the valve stem. A person having ordinary skill in the art will appreciate that the hole 196 may also be located in a different portion of the valve stem (e.g., in the valve stem head) and/or in a different position or orientation in other embodiments. As with previous examples, the stem sleeve 194 may also have at least one hole (not shown) extending therethrough. In use, the holes (not shown) of the stem sleeve 194 and the hole 196 in the valve stem are aligned when the valve stem 128 and stem sleeve 194 are nested. Next, as with previous examples, the first end of the pin of the retaining pin (not shown) may be inserted into the hole (not shown) in the stem sleeve 194 and the hole 196 in the valve stem 128 to retain the valve stem 128 with respect to the stem sleeve 194. The grips of the retaining pin (not shown) may also be configured to engage with a surface of the stem sleeve 194 in the engaged (and disengaged) position to limit rotation of the stem sleeve 194 with respect to the actuator (not shown). For example, the grips of the retaining pin (not shown) may also be configured to engage with the outer surface of the stem sleeve 194 in the engaged position to limit rotation of the stem sleeve 194 with respect to the actuator Although not shown, a person having ordinary skill in the art will appreciate that the actuator 110 of FIG. 9 may include the retention block 168 and detent 176 shown and described in FIG. 7 to retain the retaining pin (not shown) in the disengaged position. Alternatively, instead of the detent 176, the actuator may include the spring 184 shown in FIG. 8 for retaining the retaining pin in the disengaged position. Additionally, the retaining pin (not shown) used to retain the valve stem 128 with respect to stem sleeve 194 may be configured to always remain engaged with the stem sleeve 194 (e.g., the first end of the pin (not shown) remains engaged with the hole (not shown) in the stem sleeve 194 and the grips (not shown) of the retaining pin remain engaged with the exterior surface of the stem sleeve 194).

In some embodiments, instead of using the pin 150 to retain the moveable member 138 with respect to the valve stem 128 (e.g., the first end 152 of the pin 150), the retaining pin 136 may have a spade 198 that extends between the two grips 148. As shown in FIGS. 10a and 10b, the spade 198 has a substantially rectangular shape with a cutout 199. A person having ordinary skill in the art will appreciate that the shape of the spade 198 may vary in other embodiments (e.g., the spade may 198 have a circular, oval, or other polygonal shape with the cutout 199). In some embodiments, the shape of the cutout 199 corresponds to the shape of the valve stem 128 and/or to the shape of the groove(s) on the valve stem 128 or on the moveable member 138, as will be described. As is shown, a distal end of the spade is attached to the pin 150, which is attached to the grips 148. As with other embodiments, the second end 172 of the pin 150 may extend through the retention block 168 to maintain the position of the retaining pin 136 in the actuator, for arresting the motion of the retaining pin 136 away from the moveable member, and for retaining the retaining pin 136 in the disengaged position.

As is shown in FIGS. 10a and 10b, an embodiment in which the moveable member is again the female coupling portion with a recess 140 into which the valve stem head 142 is nested, the spade 198 engages with a groove 200 in the moveable member 138. As is shown in FIG. 10b, the spade 198 may also engage with a groove 202 on the valve stem 128. In some embodiments, as is shown, the groove on the valve stem is formed adjacent the valve stem head 142. In use, once the valve stem head 142 is nested in the moveable member 138, the spade 198 engages with at least the groove 200 in the moveable member 138, and the grips 148 engage with the moveable member 138 to retain the valve stem 128 with respect to the moveable member 138.

According to another embodiment, a method of assembling the hot runner system is disclosed. In some embodiments, the piston 134 of the actuator 110 is the moveable member, the female coupling portion into which the valve stem head 128, the male coupling portion, is nested. During assembly, the actuator 110 is assembled separately wherein the piston is placed in the cylinder 113, the cylinder cap is installed, the retaining pin 136 is attached to the piston (e.g., the first end 152 of the pin 150 is inserted into the hole 160 of the piston 134), and the retention block 168 is attached to the cylinder capturing the second end 172 of the pin 150. When the retaining pin 136 is pulled away from the piston 134, disengaging movement of the retaining pin 136 is stopped by the retention block 168 such that the first end 152 of the pin 150 remains engaged with the piston 134 (e.g., by maintaining the first end 152 of the pin 150 in the hole 160a of the piston 134). In this position, the actuator assembly may be placed over the valve stem 128 such that the head 142 of the valve stem 128 is inserted into the recess 140 of the piston 134. When the actuator 110 is placed over the valve stem 128, the retaining pin 136 can be pushed inwardly such that the retaining pin 136 retains the valve stem 128 with respect to the piston 134. In one embodiment, when the retaining pin 136 is pushed inwardly, the first end 152 of the pin 150 engages with the hole 158 in the valve stem head 142, retaining the valve stem 128 to the piston 134. The grips 148 of the retaining pin 136 are also engaged with the the piston 134 to prevent rotation (e.g. the exterior surface 159 of the piston 134 in the case of the FIG. 2a embodiment, or the interior indentation 299 in the hole 160 in the case of FIG. 2b embodiment). As with other embodiments, the piston 134 may also have a non-rotation feature (e.g., the D-shaped configuration of the recess 140 and the valve stem head 142) to prevent rotation of the valve stem 128 with respect to the cavity.

In the embodiments shown in FIGS. 2a, 3a and 3b, the grips 148 of the retaining pin 136 may be made of 301 spring steel, and the pin 150 may be made of 17-4 for strength, although other suitable materials may be used. The grips 148 and the pin 150 may be joined together by tungsten inert gas (TIG) welding, metal inert gas (MIG) welding, spot welding, brazing, or another suitable joining technique. Spring steel may be used to make the grips 148 such that the assembly is held to the piston (or other moveable member) and requires a force to disengage the retaining pin from the piston (or other moveable member).

In some embodiments, the force to disengage the retaining pin from the piston (or other moveable member) may be at least a 31b-force, although other forces less than or greater than the 31b-force may be used.

In some embodiments in which the grips 148 are arms extending from the pin 150 (such as shown in FIGS. 2a, 3a and 3b), the shape of the grips 148 beyond the first radius, e.g. a flare or reverse curve proximate the leading edges 153 as shown in FIGS. 3a, 7d, 10a and 10b, provides a force that acts to push the retaining pin 136 away from the piston (or other moveable member) and against the retention block 168.

In some embodiments, the force used to push the retaining pin away from the piston is a 2 lb-force, although other suitable forces for separating the retaining pin from the piston (or other moveable member) may be used. The retaining pin 136 motion away from the piston is arrested by the retention block 168. The force acting to push the retaining pin away from the piston (or other moveable member) coupled with the grips 148 prevents rotation of the grips 148 such that if the piston 134 is actuated while the retaining pin 136 is disengaged, the orientation of the retaining pin 136 relative to the piston will not change and thus the retaining pin 136 will not be damaged by the movement of the moveable member.

In some embodiments in which the grips 148 are arms extending outwardly from the pin 150, the height H of the grips 148 serves to stabilize the retaining pin against the piston (or other moveable member).

In some embodiments, the pin 150 of the retaining pin 136 is designed to be stronger than the valve stem 128 (e.g., the head 142 of the valve stem) 128 such that the valve stem 128 (e.g., the head 142 of the valve stem 128) will fracture before the pin 150 will shear should the valve stem 128 be unable to move while the piston 134 is actuated. This relationship may be reversed in other embodiments such that the pin 150 acts as a shear pin to protect the valve stem 128 if that is desired. The material choice for the pin 150 may also be changed to directly affect the shear strength of the pin 150 depending on the desired outcome. The material thickness and shape of the grips 148 may also be altered to change the desired retention force in either the engaged or disengaged position. The second end 172 of the pin 150 may be knurled or made to have a different profile if it is desired to have a special or standard tool used to engage or disengage the retaining pin 136. The second end may also be squared off to prevent rotation of the retaining pin 136.

According to another embodiment, the retaining pin 136 includes an actuating end and an engaging end. In some embodiments, the engaging end includes an member engagement portion configured to engage the moveable member 138 and an inner engagement portion configured to engage at least the valve stem 128. In some embodiments, the member engagement portion is substantially C-shaped, while, in other embodiments, the member engagement portion is substantially U-shaped and has flared ends, and in other embodiments the member engagement portion includes a ball lock. The member engagement portion may include two grips 148. In some embodiments, the member engagement portion can be configured to at least partially engage an outer surface of the moveable member 138. In some embodiments the member engagement portion can be configured to engage an inner surface of the moveable member 138. In some embodiments, the inner engagement portion includes a pin 150 extending between the two grips 148. The inner engagement portion also may include a spade 198 that extends between the two grips 148. In some embodiments, the actuating end includes a pin extending outwardly from the engaging end. The actuating end may also be adapted to be received by a retention block 168 of the actuator 110. In some embodiments, the actuating ends also includes a visual indicator 154 adapted to indicate when the retaining pin 136 is in a disengaged position.

In the previous embodiments, the valve stem 128 is shown and described as being the male coupling portion with the head 142 of the valve stem 128 being nested within the recess 140 of the moveable member 138 (e.g., the piston 134 or the stem sleeve 194), the female coupling portion. A person having ordinary skill in the art will appreciate that in any of the previous embodiments or in any other embodiment, the valve stem 128 may be configured to be the female coupling portion and the moveable member 138 may be configured to be the male coupling portion. For example, in some embodiments, the valve stem may have a recess into which the moveable member, or a protrusion extending from the moveable member is nested. In such an embodiment, the retaining pin functions as previously described, that is by extending the first end of the pin through the hole in the valve stem 128, the female coupling portion, and then through the hole in the moveable member (e.g., the piston 134 or the stem sleeve 194), the male coupling portion.

In some embodiments, each of the valve stem 128 and the moveable member 138 has a male coupling portion and a female coupling portion. In such an embodiment, the male coupling portions of the valve stem 128 and the moveable member 138 are coupled with the female coupling portions of the moveable member 138 and valve stem 128, respectively. In some embodiments, the female coupling portions include recesses into which the male coupling portions are nested, and the retaining pin 136 function as previously described to retain the male coupling portions with respect to the female coupling portions.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art. Accordingly, the foregoing description and drawings are by way of example only.

The invention claimed is:

1. A valve gated molding material distributor for an injection molding machine for passing melt into a mold cavity, the molding material distributor comprising:
   a nozzle (108) having a valve stem (128);
   an actuator (110) configured to move the valve stem (128) between a first position and a second position, the actuator (110) having a moveable member (138, 134, 194) coupleable to the valve stem (128); and
   a retaining pin (136) for coupling the valve stem (128) directly to the moveable member (138, 134, 194), wherein the retaining pin comprises grips and a pin, at least a first end of the pin extending between the grips, wherein the pin is arranged and configured to retain the valve stem to the moveable member
   wherein one of the moveable member and the valve stem comprises a male coupling portion and the other of the moveable member and the valve stem comprises a female coupling portion, the male coupling portion being nestable within the female coupling portion and wherein the retaining pin retains the male coupling portion relative to the female coupling portion,
   and wherein each of the male coupling portion and the female coupling portion has at least one hole through which the first end of the pin extends, the at least one hole of the male coupling portion being aligned with the at least one hole of the female coupling portion when the male and female coupling portions are nested and wherein the pin is extendable transversely through the holes of the nested male and female coupling portions,
   and wherein a leading edge of each grip is configured to facilitate engagement between the grips and the exterior surface of the female coupling portion, and wherein the leading edge is a flared end of the grip that facilitates outward camming of the grip upon contact with the female coupling portion.

2. The valve gated molding material distributor according to claim 1, wherein the retaining pin (136) travels with the coupled moveable member (138, 134, 194) and valve stem (128) between the first and second positions.

3. The valve gated molding material distributor according to claim 1, wherein the valve stem (128) comprises the male coupling portion and the moveable member (138, 134, 194) comprises the female coupling portion, wherein the male coupling portion is the head of the valve stem and the female coupling portion is a recess in a downstream end of the moveable member.

4. The valve gated molding material distributor according to claim 3, wherein the female coupling portion further comprises at least one groove (200) on the moveable member (138, 134) for engaging the retaining pin (136).

5. A valve gated molding material distributor for an injection molding machine for passing melt into a mold cavity, the molding material distributor comprising:
   a nozzle having a valve stem;
   an actuator configured to move the valve stem between a first position and a second position, the actuator having a moveable member coupleable to the valve stem; and
   a retaining pin for coupling the valve stem directly to the moveable member, wherein the retaining pin comprises grips and a pin, at least a first end of the pin extending between the grips, wherein the pin is arranged and configured to retain the valve stem to the moveable member, wherein the first end (152) of the pin (150) is adapted to be engaged with the at least one hole (160) of the female coupling portion when the retaining pin (136) is in a disengaged position, the male coupling portion adapted to be removable from the female coupling portion when the retaining pin (136) is in the disengaged position, and wherein the grips (148) are adapted to be engaged with an exterior surface (162, 159) of the female coupling portion when the retaining pin (136) is in the disengaged position to prevent rotation.

6. The valve gated molding material distributor according to claim 5, wherein the actuator (110) further comprises a retention block (168), the retention block (168) configured to retain the retaining pin (136) when the retaining pin (136) is in a disengaged position.

7. The valve gated molding material distributor according to claim 6, wherein the retention block (168) comprises at least one of a detent (176) and a spring (184) for holding the retaining pin (136) in the disengaged position.

8. The valve gated molding material distributor according to claim 1, wherein the retaining pin (136) comprises a visual indicator (154) adapted to indicate when the retaining pin (136) is in a disengaged position.

9. A valve gated molding material distributor for an injection molding machine for passing melt into a mold cavity, the molding material distributor comprising:
   a nozzle having a valve stem;
   an actuator configured to move the valve stem between a first position and a second position, the actuator having a moveable member coupleable to the valve stem; and
   a retaining pin for coupling the valve stem directly to the moveable member, wherein the retaining pin comprises at least one grip and a pin, wherein the pin is arranged and configured to retain the valve stem to the moveable member,
   wherein one of the moveable member and the valve stem comprises a male coupling portion and the other of the moveable member and the valve stem comprises a female coupling portion, the male coupling portion being nestable within the female coupling portion and wherein the retaining pin retains the male coupling portion relative to the female coupling portion,
   and wherein the retaining pin (136) comprises a grip (148) on a pin (150), wherein the grip is a ball lock.

* * * * *